United States Patent [19]

Lentz et al.

[11] Patent Number: 4,929,737

[45] Date of Patent: May 29, 1990

[54] HYDROGENATION OF HALONITROAROMATIC COMPOUNDS

[75] Inventors: Carl M. Lentz, Kingsport; Edward T. Mullins, Church Hill; Charles L. Gibson, Kingsport, all of Tenn.

[73] Assignee: Eastman Kodak Company, Rochester, N.Y.

[21] Appl. No.: 151,726

[22] Filed: Feb. 3, 1988

[51] Int. Cl.$^5$ .................. C07D 231/00; C07D 127/19; C07D 143/80; C07D 103/22

[52] U.S. Cl. .................................... 548/365; 564/184; 564/47; 564/86; 564/417

[58] Field of Search .................... 564/417, 47, 86, 184; 548/365

[56] References Cited

U.S. PATENT DOCUMENTS 3,929,891 12/1975 Habig et al. ........................ 564/417
4,248,799 2/1981 Drake .................................. 564/491

FOREIGN PATENT DOCUMENTS 1498722 3/1975 United Kingdom ................ 564/417

OTHER PUBLICATIONS

"The Hydrogenation of Aromatic Nitro Compounds to Aromatic Amines" by Axel M. Stratz.

Primary Examiner—Douglas W. Robinson
Assistant Examiner—Zohreh A. Fay
Attorney, Agent, or Firm—J. Frederick Thomsen; William P. Heath, Jr.

[57] ABSTRACT

Disclosed is an improved process for the preparation of haloaromatic amines by the catalytic hydrogenation of halonitroaromatic compounds in the presence of a chromium-containing Raney cobalt catalyst. The catalyst gives good hydrogenation rates while minimizing formation of dehalogenated by-products.

5 Claims, No Drawings

HYDROGENATION OF HALONITROAROMATIC COMPOUNDS

This invention pertains to the catalytic hydrogenation of halonitroaromatic compounds to obtain the corresponding haloaromatic amine. More particularly, this invention pertains to the hydrogenation of halonitroaromatic compounds in the presense of a chromium containing, Raney cobalt catalyst.

Problems encountered in the preparation of haloaromatic amines by the catalytic hydrogenation of halonitroaromatic compounds include poor catalyst activity and selectivity which results in incomplete or partial conversion of the starting material to the desired haloaromatic amine product and dehalogenation of the starting material. Known processes for catalytically hydrogenating halonitroaromatic compounds give less than optimum yields and require time consuming and costly purification procedures to obtain the desired haloaromatic amine in a degree of purity required for its use in the preparation of many compounds such as pharmaceutical and photo graphic chemicals.

The use of various catalysts in attempts to overcome the above mentioned problems has been reported extensively in the literature such as, for example, U.S. Pat. Nos. 2,772,213, 2,791,613, 3,051,753 and 3,683,025; German Patents No. 1,493,629 and 1,543,955; British Patent No. 1,453,966; Ann. NY Acad. Sci., 145, 58 and 108 (1965); J. Amer. Chem. Soc., 76, 1519 (1954) and 87,2767 (1965) and Canad. J. Chem.. 36,238 (1958). The catalysts described in these references are concerned with special cases and do not have general application. Platinum on activated carbon an activated nickel have been used in the presence of catalyst inhibitors such as thiophene, triphenylphosphite (U.S. Pat. No. 3,474,144), polyamines (German Patent No. 2,308,105 and U.S. Pat. No. 3,158,646), magnesium oxide (U.S. Pat. No. 3,073,865), thioesters (German Patent No. 2,549,900) and phosphorous acid and its derivatives (U.S. Pat. No. 4,020,107 . However, such catalysts do not give consistent results, especially in batch operation using not only different halonitroaromatic starting materials but varying grades of the same starting materials.

High selectivities of haloaromatic amines have been reported using Platinum sulfide (U.S. Patent 3,350,450) and sulfided platinum on carbon (U.S. Patents 3,761,425 and 3,929,891). The use of such sulfur modified catalysts is disadvantageous due to the loss of the sulfiding agent off the catalyst which causes its selectivity to change and introduces another impurity into the product.

We have discovered that haloaromatic amines can be obtained in excellent yields by the hydrogenation of the corresponding halonitroaromatic compounds in the presence of chromium modified or chromium-promoted Raney cobalt catalyst which also may contain nickel. The chromium containing Raney cobalt catalyst exhibits good to excellent activity while minimizing dehalogenation resulting in improved yields of haloaromatic amines of improved purity.

Our improved process thus entails the preparation of a haloaromatic amine by the hydrogenation of a nitrohaloaromatic compound in the presence of a catalytic amount of chromium promoted Raney cobalt under hydrogenation conditions of temperature and pressure. The process may be advantageously used to hydrogenate a wide variety of nitroaromatic halides to the corresponding haloaromatic amines. The nitrohaloaromatic reactants contain both a nitro group and a halogen atom attached to nuclear carbon atoms of the same or different carbocyclic aromatic groups such as a benzene or naphthalene ring. Although the process may be used advantageously for the hydrogenation of nitroaromatic halides in general such as, for example, nitroaromatic bromides and nitroaromatic iodides, nitroaromatic chlorides are the most common reactants.

The nitroaromatic halide reactants and their corresponding haloaromatic amine products may be represented by the formulas:

$$R^1—A—NO_2 \qquad R^1—A—NH_2$$

wherein A is an aromatic ring attached to the nitro group by a nuclear carbon atom and $R^1$ is an organic radical and wherein at least one nuclear carbon atom of aromatic ring A or of an aromatic ring of organic radical $R^1$ is substituted with a halogen atom, preferably a chloride atom. Organic ring A may bear additional substituents such as hydroxy, alkyl, alkoxy, aryloxy, formyl, alkanyl, cycloalkanoyl, aroyl, alkanoyloxy, cycloalkanoyloxy, aroyloxy, alkylsulfonyl, cycloalkylsulfonyl, arylsulfonyl, alkanoylamino, cycloalkanoylamino, aroylamino, alkylsulfonamino, cycloalkylsulfonamido, arylsulfon amido, alkoxycarbonyl, cycloalkoxycarbonyl, aryl oxycarbonyl, carbamoyl, sulfamoyl, and substituted amino. These substituents also are representative of those which $R^1$ can represent. The alkyl groups and alkyl moieties typically may be straight or branch chain, unsubstituted or substituted alkyl of up to about 20 carbon atoms. Examples of such alkyl groups include methyl, ethyl, propyl, 2 methylpropyl, 1,1-dimethylpropyl, hexyl, octyl, 2-ethylhexyl, decyl, dodecyl, hexadecyl, etc. The cycloalkyl groups may be unsubstituted or substituted cycloalkyl of about 5 to 7 carbon atoms such as cyclopentyl, cyclohexyl, cycloheptyl and the like. The aryl groups are carbocyclic, unsubstituted or substituted aryl such as phenyl or naphthyl. The carbamoyl and sulfamoyl groups may be unsubstituted or substituted, for example, with alkyl, cycloalkyl, or aryl. The substituted amino groups may bear one or two alkyl, cycloalkyl, aryl or heterocyclic groups.

Preferred reactants and their corresponding products have the formulas:

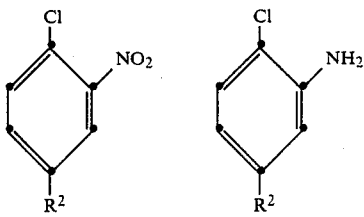

wherein $R^2$ is alkoxycarbonyl of up to about 20 carbon atoms, alkylsulfamoyl of up to about 20 carbon atoms, alkanoylamino of up to about 20 carbon atoms or alkanoylamino of up to about 10 carbon atoms substituted with phenoxy, alkyl phenoxy or dialkylphenoxy in which each alkyl group has up to about 10 carbon atoms;

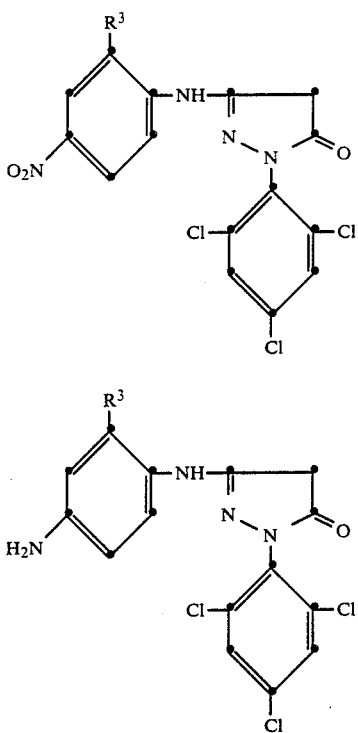

wherein R³ is hydrogen or chloro;

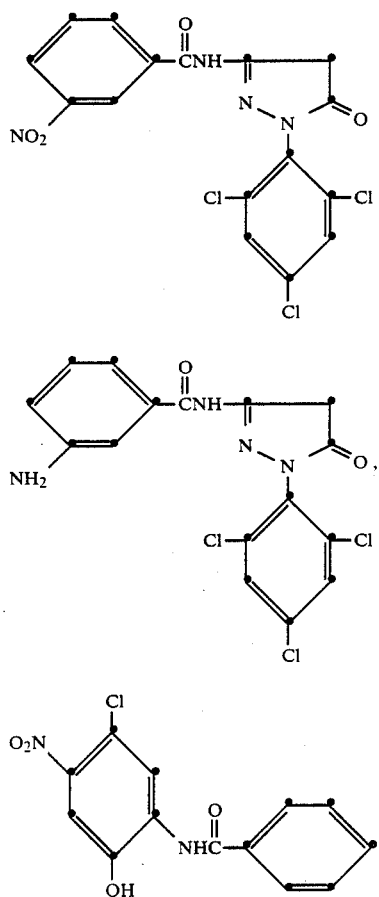

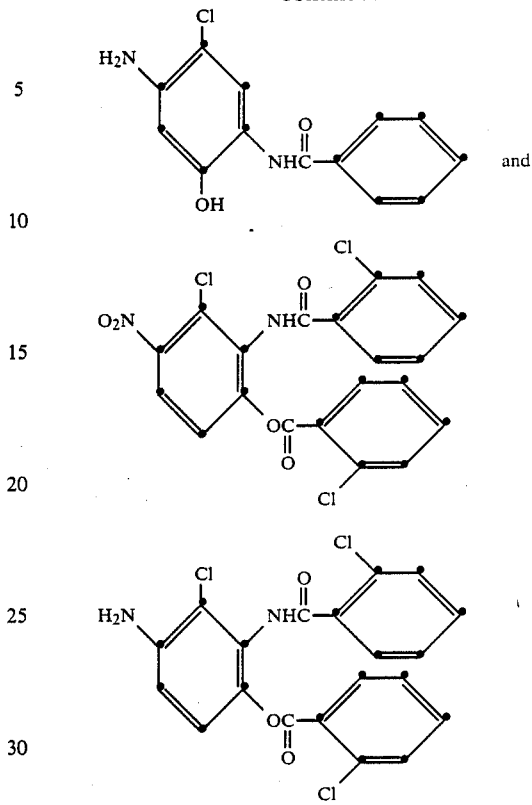

The catalyst utilized in the hydrogenation process provided by our invention is obtained by conventional procedures used in the preparation of Raney catalysts. Generally an alloy comprising about 50 weight percent aluminum and varying amounts of cobalt, chromium, and, optionally, nickel is prepared, then ground to a desired particle size and finally treated with aqueous sodium hydroxide to extract a portion of the aluminum and thereby activate the catalyst. Typically, after activation the weight ratio of the catalytically active metals, e.g., cobalt, chromium, and, optionally, nickel, to aluminum is in the range of about 7:3 to 8:2.

The chromium-promoted Raney cobalt catalyst used in the hydrogenation process contains about 1 to 10 weight percent chromium, preferably about 2 to 5 weight percent. About 2.5 weight percent is believed to give the best results, i.e., catalytic activity and selectivity. The catalyst may also contain up to about 5 weight percent nickel and preferably contains about 1 to 4, optimumly about 2, weight percent nickel.

The extraction temperature used in the preparation of the active catalyst may be in the range of about 40° to 180° C., preferably in the range of about 60° to 120° C. Catalysts with superior activity are obtained when the extraction temperature is in the range of about 70° to 90° C. We have found that there is an apparent correlation between catalyst activity and the amount of cobalt metal, i.e., (Co°) present on the surface of the catalyst. The amount of surface cobalt metal is determined by the equation.

Surface Co° = [(Co°)/(Co)][(Co)/(Co)+(Cr)][SA]

wherein (Co°) is cobalt metal, (Co) is total cobalt and (Cr) is total chromium at the surface of the catalyst determined by electron spectroscopy using a PHI Model 550 ESCA/SAM spectrometer and SA is the BET surface area in square meters per gram using a Model QS11 surface area analyzer made by Quantichrome. Factors which give high Surface Co° values are the use of a lower extraction temperature in activating the catalyst and the presence of low amounts of chromium.

The amount of catalyst used in our novel process can be varied substantially depending on several factors such as, for example, the activity of the particular catalyst, the reaction conditions, i.e., temperature and Pressure, employed, the reaction time required, the nitroaromatic halide to be hydrogenated and the mode of operation employed. While catalyst concentrations in the range of 0.01 to 10.0 percent based on the weight of the nitroaromatic halide reactant may be used, normally the concentration will be in the range of about 0.1 to 5.0 percent.

The hydrogenation conditions of temperature and pressure similarly can be varied over a wide range. For example, temperature and pressure are inter dependent to some extent and increasing one may permit the use of lower levels of the other. The particular temperature and/or pressure used can also depend on catalyst concentration, the reactant to be hydrogenated, mode of operation as well as the reaction time that is desired. Temperatures in the range of about 25° to 200° C. may be used with the range of about 25° to 125° C. being preferred. Pressures of 0 to 2,000 psig may be employed although the hydrogenation is more often conducted at Pressures in the range of about 100 to 1,000 psig. Generally, the best results are obtained when using low temperatures, e.g., 50° to 100° C., and high pressures, e.g., 600 to 800 psig.

The hydrogenation process is carried out in an inert solvent for the nitroaromatic halide reactant. The solvent preferably is a primary or secondary alkanol having up to about 4 carbon atoms, especially methanol, ethanol and isopropanol. Co-solvents such as dimethylformamide, dimethylacetamide and tetra hydrofuran may be used in combination with an alkanol when required by the solubility characteristics of the reactant. The solubility of sparingly soluble reactants which have an acidic hydrogen can be enhanced by including a base in the initial reaction mixture. Other solvents which may be employed include esters such as methyl and ethyl acetate, ethers such as tetrahydrofuran and diisopropyl ether and, to a lesser extent, hydrocarbons such as toluene or benzene.

Our novel process can be carried out as a batch process, a semi continuous process or a continuous process. In batch operation a slurry of the catalyst in an inert solvent in which the reactant has been dissolved is fed to a pressure vessel equipped with means for agitation. The pressure vessel then is pressurized with hydrogen to a predetermined pressure and then is heated to bring the reaction mixture to the desired temperature. After the hydrogenation is complete the reaction mixture is removed from the pressure vessel, the catalyst is separated by filtration and the product is isolated, for example, by crystallization followed by filtration. Continuous operation can utilize a fixed catalyst bed using a larger particle size of catalyst. The catalyst bed may be located in a pressure vessel and a solution of the reactant slowly fed continuously above the bed at elevated temperature and pressure and a solution of the haloaromatic amine removed at the bottom of the pressure vessel. Another mode of continuous operation utilizes a slurry of catalyst in an agitated pressure vessel which is fitted with a filter leg to permit continuous removal of a solution of product in an inert solvent. In this manner a reactant solution can be continuously fed to and product solution continuously removed from an agitated pressure vessel containing a slurry of the catalyst.

The process provided by our invention is further illustrated by the following examples.

EXAMPLES 1-6

N-(4-chloro-3-nitrophenyl]-4-(2,4-bis[1,1-dimethylpropyl]phenoxy)butanamide (Reactant) is hydrogenated to produce N (3 amino 4-chlorophenyl)-4-(2,4-bis[1,1-dimethylpropyl phenoxy)butanamide (Product) using chromium containing Raney catalysts containing varying amounts of chromium and extracted at different temperatures. The catalysts employed in the examples are described below. The chromium content of the catalyst is the approximate weight percent of chromium based on total catalyst weight after extraction. The extracted catalysts contained approximately 20-30 weight Percent aluminum and 1.5 to 2.5 weight percent nickel, the remainder being cobalt.

| Example | Chromium Content, Wt. % | Extraction Temperature. °C. |
|---|---|---|
| 1 | 2.0 | 100-110 |
| 2 | 4.0 | 100-110 |
| 3 | 6.0 | 100-110 |
| 4 | 2.0 | 65-75 |
| 5 | 4.0 | 65-75 |
| 6 | 6.0 | 65-75 |

In each of the examples the catalyst (5.0 g) is mixed with a solution of Reactant R-I (175.0 g) in methanol (271 mL) in a high pressure, one liter autoclave. The autoclave is sealed, pressurized with hydrogen to 750 psig and then heated to 60° C. Hydrogen uptake is observed by monitoring pressure change. When the pressure becomes constant, the reaction mixture is maintained at 60° C. for an additional hour and the autoclave is vented. A sample of the reaction mixture is taken and analyzed by liquid chromatography and the relative amounts of Product, Reactant, dechlorinated compound (Dechloro Compound) and partially hydrogenated compound (Hydroxylamine) are determined. The reaction mixture then is discharged and clarified to remove the catalyst. Water is added to the filtrate and the Product is isolated by filtration.

The results obtained and the hydrogenations times employed in each of the preceding examples are shown in Table I. The results reported for Example C are obtained when a Raney nickel catalyst is used in the above described procedure.

TABLE I

| Ex. | Product | Reactant | Dechloro Compound | Hydroxylamine | Hydrogenation Time, Hours |
|---|---|---|---|---|---|
| 1 | 97.0 | 0.1 | 0.6 | 0.8 | 3.0 |
| 2 | 97.1 | 0.1 | 0.3 | 0.6 | 3.0 |
| 3 | 94.0 | 0.4 | 0.1 | 1.1 | 8.0 |
| 4 | 98.1 | 0.1 | 0.1 | 0.6 | 1.5 |
| 5 | 98.2 | 0.1 | 0.1 | 0.6 | 2.5 |
| 6 | 97.3 | 0.1 | 0.1 | 0.9 | 3.0 |
| C | 91.5 | 0.3 | 7.5 | 0.7 | 2.0 |

EXAMPLE 7

Using the procedure described above and 5.0 g of a chromium-containing Raney cobalt catalyst containing about 20-30 weight percent aluminum, 1.5 to 2.5 weight percent nickel and the remainder cobalt, 2-benzamido 4-chloro 5-nitrophenol is hydrogenated for a total of 4 hours to obtain the corresponding amine, 5-amino 2-benzamido 4-chlorophenol. Analysis of a sample of the reaction mixture taken and analyzed in accordance with the procedure used in the preceding example, show that the purity of the product is 98.4 percent and the presence of 0.1 percent of dechlorinated by product. The azo, azoxy and hydroxylamine intermediate products are soluble in the final filtrate and thus are easily removed from the product. No starting material is detected.

EXAMPLE 8

Dodecyl 4-chloro 3-nitrobenzoate is hydrogenated according to the procedure described in Example 7. The desired amine, dodecyl 3-amino-4-chlorobenzoate, is obtained in a purity of 99.5 percent and the amount of dechlorinated by product is 0.2 weight percent.

EXAMPLE 9

The procedure of Example 7 is repeated except that the nitroaromatic halide employed is N-hexadecyl-4-chloro-3-nitrobenzenesulfonamide. Analysis of the final reaction mixture shows that the amine product, N hexadecyl-3-amino 4 chlorobenzenesulfonamide, is obtained in a purity of 99.2 percent and the presence of 0.1 percent dechlorinated material. Conversion of the starting material is 100 percent.

EXAMPLE 10

The catalyst (6.0 g) used in Example 7 is mixed with a solution of 1-(2,4,6 trichlorophenyl)-3-(2-chloro-5-nitrophenylamino)-2-pyrazolin 5 one (134.0 g) in methanol (343 mL) and dimethylformamide (10.5 g) in a high pressure, one liter autoclave. The autoclave is sealed, pressurized with hydrogen to 800 psig and then heated to 55° C. When hydrogen uptake ceases (approximately 2 hours), the autoclave is cooled to 30° C. and vented. A solution of 50% aqueous sodium hydroxide (30.0 %) and water (50.0 g) is then added to the autoclave and the pressure is raised to 400 psig and maintained at 400 psig and 30° C. for two hours. The autoclave is then vented and a sample of the reaction mixture is taken for liquid chromatography analysis. The catalyst is filtered off, acetic acid is added to the filtrate until it has a pH of 4 and the amine product, 1-(2,4,6-trichlorophenyl)-3-(5-amino 2-chlorophenylamino) 2-pyrazolin-one, is separated by Filtration. The liquid chromatography analyses showed that the product is 99.9 percent pure and contains no dechlorinated by product.

EXAMPLE 11

The procedure of Example 10 is repeated using 1-(2,4,6-trichlorophenyl) 3 (3 nitrobenzamido) 2-pyrazolin 2-one as the nitroaromatic halide. Liquid chromatography analysis showed that the purity of the product is 98.9 percent and that the amount of dechlorinated by-product is 0.1 percent.

The invention has been described in detail with particular reference to preferred embodiments there of, but it will be understood that variations and modifications can be effected within the spirit and scope of the invention.

We claim:

1. Process for the preparation of a haloaromatic amine which comprises hydrogenating the corresponding halonitroaromatic compound in the presence of a catalytic amount of a chromium containing Raney cobalt catalyst under hydrogenation conditions of temperature and pressure.

2. Process according to claim 1 for the preparation of a haloaromatic amine having the formula $R^1$-A-$NH_2$ which comprises hydrogenating a nitroaromatic halide having the formula $R^1$-A-$NO_2$ in the presence of a catalytic amount of a Raney cobalt catalyst containing about 1 to 10 weight percent chromium and about 1 to 4 weight percent nickel, wherein A is an aromatic ring attached to the nitro or amino group by a nuclear carbon atom and $R^1$ is an organic radical and wherein at least one nuclear carbon atom of aromatic ring A or of an aromatic ring or organic radical $R^1$ is substituted with a halogen atom.

3. Process according to claim 2 wherein the nitro aromatic halide and the haloaromatic amine prepared therefrom have the formulas

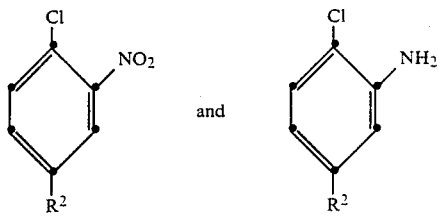

wherein $R^2$ is alkoxycarbonyl of up to about 20 carbon atoms, alkylsulfamoyl of up to about 20 carbon atoms, alkanoylamino of up to about 20 carbon atoms or alkanoylamino of up to about 10 carbon atoms substituted with phenoxy, alkylphenoxy or dialkylphenoxy in which each alkyl group has up to about 10 carbon atoms;

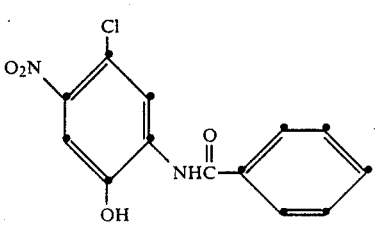

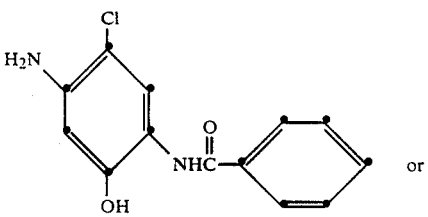

or

-continued

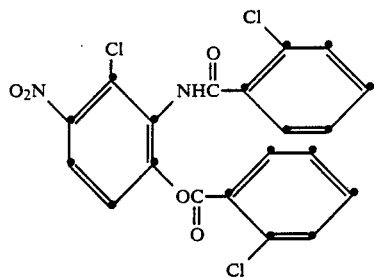

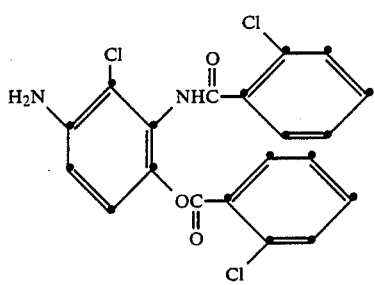

4. Process according to claim 2 wherein the nitroaromatic halide and the haloaromatic amine prepared therefrom have the formulas

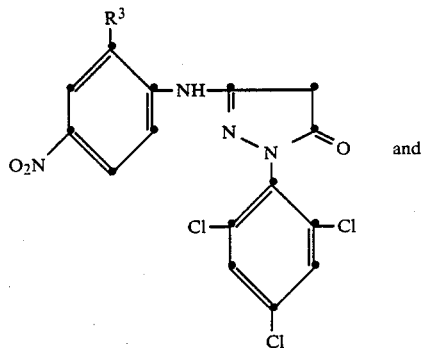

-continued

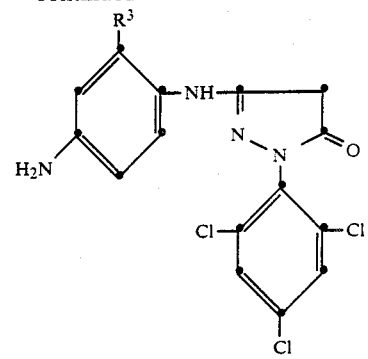

wherein R³ is hydrogen or chloro; or

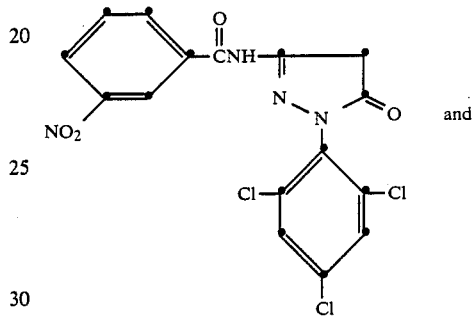

and

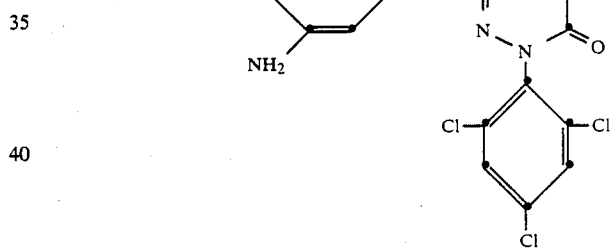

5. Process according to any of claims 1-4 wherein the Raney cobalt catalyst contains about 2-5 weight percent chromium and about 2 weight percent nickel; and the process is carried out at a temperature of about 25° to 125° C. and a pressure of about 100 to 1000 psig in the presence of a primary or secondary alkanol containing up to about 4 carbon atoms.

* * * * *